(12) United States Patent
Villettaz et al.

(10) Patent No.: US 6,397,658 B1
(45) Date of Patent: Jun. 4, 2002

(54) METHOD AND EQUIPMENT FOR MEASURING GLOBAL VOLATILE SUBSTANCES

(75) Inventors: Jean-Claude Villettaz, Sion; Jean-Luc Luisier, Conthey; Ramin Azodanlou, Montreux, all of (CH)

(73) Assignee: Brechbuhler AG (CH)

( * ) Notice: Subject to any disclaimer, the term of this patent is extended or adjusted under 35 U.S.C. 154(b) by 0 days.

(21) Appl. No.: 09/554,592

(22) PCT Filed: Nov. 12, 1998

(86) PCT No.: PCT/CH98/00484

§ 371 (c)(1),
(2), (4) Date: May 15, 2000

(87) PCT Pub. No.: WO99/26063

PCT Pub. Date: Mar. 27, 1999

(30) Foreign Application Priority Data

Nov. 15, 1997 (CH) ................................................. 2628/97

(51) Int. Cl.⁷ ............................ G01N 7/00; G01N 37/00
(52) U.S. Cl. .................. 73/19.12; 73/23.34; 73/863.21; 422/69
(58) Field of Search ............................. 73/61.59, 61.77, 73/64.56, 19.12, 23.34, 863.12, 863.21, 863.23, 64, 44; 422/69, 88, 89

(56) References Cited

U.S. PATENT DOCUMENTS

| | | | | | |
|---|---|---|---|---|---|
| 4,003,257 | A | * | 1/1977 | Fletcher et al. | 73/19.02 |
| 4,102,201 | A | * | 7/1978 | Trine et al. | 73/863.21 |
| 4,351,802 | A | * | 9/1982 | Baylis et al. | 422/89 |
| 4,563,893 | A | * | 1/1986 | Tanyolac et al. | 73/23.34 |
| 4,718,268 | A | * | 1/1988 | Reid et al. | 73/19.01 |
| 5,469,369 | A | * | 11/1995 | Rose-Pehrsson et al. | 702/27 |
| 5,496,741 | A | * | 3/1996 | Pawliszyn | 436/163 |
| 5,522,918 | A | * | 6/1996 | Shiramizu | 73/19.02 |
| 5,585,575 | A | * | 12/1996 | Corrigan et al. | 73/863.21 |
| 5,814,474 | A | * | 9/1998 | Berndt | 435/34 |
| 5,965,803 | A | * | 10/1999 | Chinn, Jr. et al. | 73/23.34 |
| 6,042,787 | A | * | 3/2000 | Pawliszyn | 422/69 |
| 6,272,937 | B1 | * | 8/2001 | Mengel et al. | 73/863.21 |

FOREIGN PATENT DOCUMENTS

EP         0730143 A2   *   9/1996

* cited by examiner

*Primary Examiner*—Hezron Williams
*Assistant Examiner*—Michael Cygan
(74) *Attorney, Agent, or Firm*—Bachman & LaPointe, P.C.

(57) ABSTRACT

Measurement of volatile substances in a global manner with no prior separation of the different compounds, wherein the volatiles produced are collected by adsorption on an adsorbent surface, the collected substances are next desorbed directly in a detector, or desorbed and conveyed by means of an inert gas through a capillary tube to a detector, for analysis of the signals obtained.

10 Claims, 4 Drawing Sheets

METHOD AND EQUIPMENT FOR MEASURING GLOBAL VOLATILE SUBSTANCES

BACKGROUND OF THE INVENTION

The invention concerns a method and a device for measuring volatile substances in a global manner, with no prior separation of the different compounds. By "global volatiles" it is desired to signify that it is not necessarily a question of all the volatiles, but particularly a representative fraction of the set of volatiles released by an object. These volatile substances generally constitute the smell of a food or of an object. The measurement of the smell of a food or of an object in its global form represents a substantial advantage both quantitatively (intensity of the smell) and qualitatively (nature of the compounds constituting the smell). Although it is possible, as far, of course, as the key substances are known accurately, to quantitatively analyze the compounds constituting the aromatic profile of a product, it was not possible, until the development and perfecting of the techniques described below, to evaluate the volatile fraction in its global form. In the full assurance of this established fact, in the light of the results which have been obtained by virtue of the present invention, it can be considered that it is now possible to measure and quantitatively analyze, in a reproducible and reliable manner, this notion of "fragrance".

SUMMARY OF THE INVENTION

The object of the invention is to create a method and a device of the type cited at the beginning which make it possible to obtain signals which are highly reproducible and also in agreement with the results of the sensory analysis. The object of the invention is resolved according to the present invention. The method of the present invention measures volatile substances in a global manner, with no prior separation of the different compounds, wherein the volatiles produced are collected by adsorption on adsorbent surfaces, the collected substances are next described directly in a detector, or desorbed and conveyed by means of an inert gas through a capillary tube which does not separate, or separates very little, to a detector, for a mathematical and/or statistical analysis of the signals obtained. The device of the present invention includes a head space for releasing the volatile substances, a system for collecting these volatile substances, a desorption system adapted to the collection system, a detection system and an evaluation system for interpreting the signals obtained.

The novelty of the invention consists of collecting volatiles, desorbing the molecules collected, transferring them without separating them and quantifying them by means of detectors. The diversity of the signals is obtained either by varying the sensors, or by varying the detection capabilities.

These concepts can be extended to volatile substances in solution by adsorption of these substances on sensors.

With the aim of quantitatively analyzing the global volatiles, with no prior separation of the different compounds, the idea arose of collecting these substances on a membrane, then desorbing this membrane directly in a detector. Most surprisingly, the signal delivered by the detector proved to be not only highly reproducible but also in perfect agreement with the results of the sensory analysis.

This technique therefore fully meets the expectations of the numerous researchers working in this field. In a recent publication dated March 1997, published in No. 129 of the CTIFL (Interbranch Technical Committee on Fruit and Vegetables), relating to the gustatory quality of peaches and nectarines, the authors (Danielle Scandella, Etienne Krauteler, Sophie Vénien) deeply regret that the measurement of global volatiles is still not possible "The physico-chemical measurements of firmness, sugar and acidity are not sufficient on their own to identify quality. The notion of fragrance, very important, is still not detectable by a device."

BRIEF DESCRIPTION OF THE DRAWINGS

The present invention will be more readily understandable from a consideration of the accompanying drawings, wherein.

DETAILED DESCRIPTION OF PREFERRED EMBODIMENTS

Figure 1:
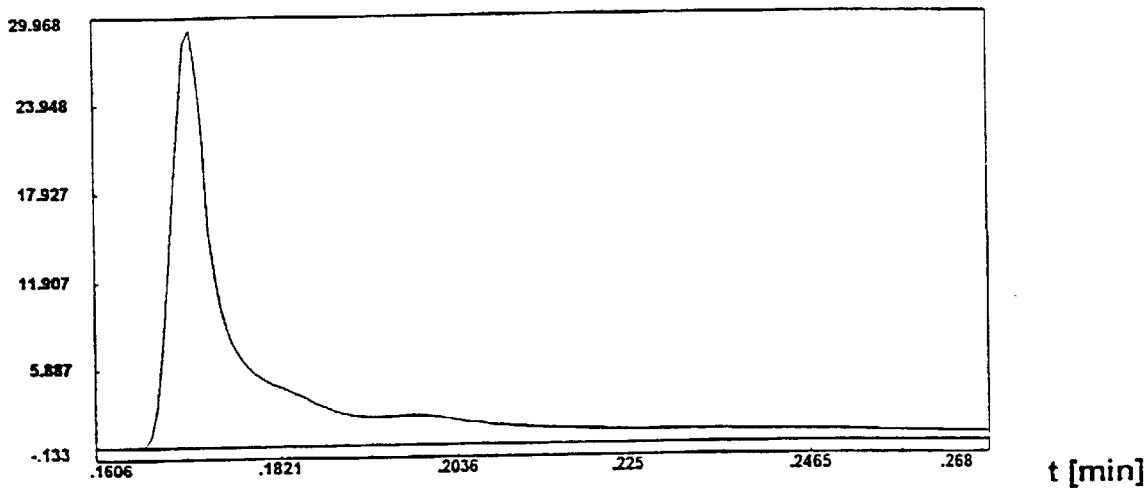
FIG. 1 is a graph of the signal obtained from a sensor showing the amplitude A in millivolts (mV) as a function of the time t in minutes.

The device being proposed is composed of five logical parts, certain of which can be combined at the time of physical construction: (FIGS. 1 and 7)

1. A system for producing a reproducible head space. This is a system, either automated or manual, making it possible to release, into a container, a head space containing the aroma of the object it is wished to analyze.
2. A system for collecting from this head space: SPME (Solid Phase Micro Extraction), systems such as "purge and trap", "thermal desorption tube", adsorbent membrane, etc.
3. A system of thermal desorption of what has been collected, adapted to the collection system. An inert gas conveys the desorbed volatiles to the detector.
4. A detection system. Universal detectors like the flame ionization detector, the electron capture detector, the thermal conductivity detector, the differential resistivity detector, the flame photometry detector and the mass spectrometry detector can be distinguished.
5. A system of evaluation based on a mathematical interpretation of the signal. The interpretation is based, on the one hand, on the area of the signal, which is a measure of the total quantity of desorbed volatiles, and, on the other hand, on the profile of the signal over time, which is in keeping with the quality of the signal. When the detector is a spectrometer, the mass spectrogram forms part of the signal.

In summary, there will therefore be the following elements (principle of the system for measuring global volatiles):

System for producing volatiles in a head space
Collection of the volatiles by adsorption
Desorption of the volatiles and conveying by means of a gas
Global detection
Interpretation (mathematical and statistical) of the signals obtained

EXAMPLES

These examples represent a few applications using various collection, desorption and detection systems. The examples cited do not cover, by a long way, all the possible applications of the present invention, but give a general picture of its possibilities and summarize the main results obtained.

1. SYSTEMS FOR COLLECTING GLOBAL VOLATILES

The volatile substances, released in the head space system, will be collected on adsorbent surfaces. These surfaces can be for example SPMEs (Solid Phase Micro Extraction), adsorbent tubes, "purge and trap" adsorbent systems, or surfaces modified chemically so as to obtain an optimum adsorption of the volatiles for application of substances known to persons skilled in the art. Through heating, these surfaces release the collected volatile substances, which are next conducted into the detector by being conveyed by means of an inert gas.

Detailing the systems for collecting volatiles, there are thus found systems based on:

a. SPME (Solid Phase Micro Extraction) technology. It is known that SPME lends itself well to quantitative analyses. It allows volatiles to be adsorbed;

b. systems known in gas chromatography by the names "purge and trap" and "head space";

c. membranes. The head space to be analyzed can be adsorbed at the surface of membranes of various structures such as those used for electronic noses.

2. DESORPTION AND SALTING OUT SYSTEMS

The aim of desorption is to release the volatile substances from the collection system and to transport them to the detector. There will be a number of types of desorbers:

a. SPME: when, for collecting the volatiles, an SPME is used, an injector with a septum can be used as a desorber. Desorption can either be carried out directly in the flow of carrier gas or in the absence of such a flow and the latter restored after desorption.

b. purge and trap and head space systems: in this case the desorption system used is generally developed by the manufacturer of the head space or purge and trap system.

The desorbed volatile substances are next conducted through a tube into the detector, with no separation. A flow of inert gas provides the transport of the desorbed volatiles (salting out system).

3. APPLICATIONS

The device used is composed of a sensor made from an SPME, a desorber composed of an injector with a septum, directly connected to a flame ionization detector by a capillary which is not, or is very little, absorbent. Interpretation is performed by measuring the area of the signal. An example of the signal obtained is given in FIG. 1 showing the amplitude A in millivolts (mV) as a function of the time t in minutes (min).

A) REPRODUCIBILITY OF THE MEASUREMENT

Figure 2:
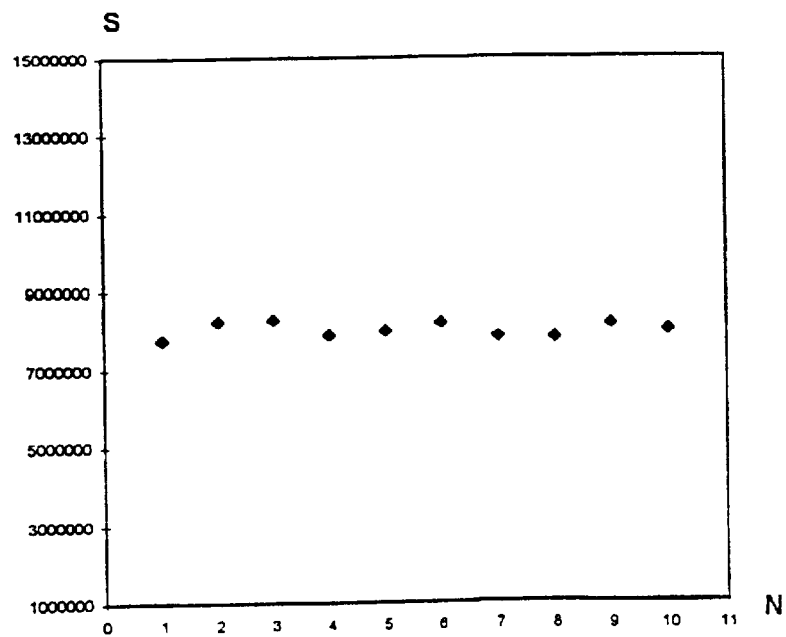
FIG. 2 shows the area of the signals S as a function of the test numbers N 1 to 10.

In a 1 litre flask, maintained at a constant temperature of 20° C., a given quantity (200 g) of strawberries was placed. After stabilization of the head space for half an hour, an SPME (Polydimethylsiloxane 100 μm, Supelco Co., Bellefonte, Pa.) is immersed in this head space, through a septum, for a duration of 5 minutes. The SPME is next desorbed in an injector with a septum maintained at 200° C. during the whole measurement. A 5 ml/min current of helium conveys the volatile substances through a capillary tube (length 200 mm, internal diameter 0.1 mm; No. 160–2630 J&W, New Brighton (Minn.), pressure of the helium: 150 kPa). The temperature of the injector is maintained at 200° C. The detector used is a flame ionization detector (FID) from the firm Carlo Erba, the working temperature is maintained constant at 250° C. The signal, measured as the area of a peak by means of the Chrom Card program (Fisons, Milano), is highly reproducible (Table 1). FIG. 2 depicts the area of the signals S as a function of the test numbers N 1 to 10. It illustrates clearly the reproducibility of the measurement.

TABLE 1

| Areas of the signals and statistical evaluation of the results | |
|---|---|
| Test number | Area of the signal |
| 1 | 7738041 |
| 2 | 8233225 |
| 3 | 8258000 |
| 4 | 7860169 |
| 5 | 7950000 |
| 6 | 8164000 |
| 7 | 7797004 |
| 8 | 7772511 |
| 9 | 8140915 |
| 10 | 7977580 |
| Mean | 7951739 |
| Standard deviation | 155972 |
| Coefficient of variation | 1.96% |

B) HETEROGENEOUSNESS OF A BATCH OF STRAWBERRIES

Figure 3:
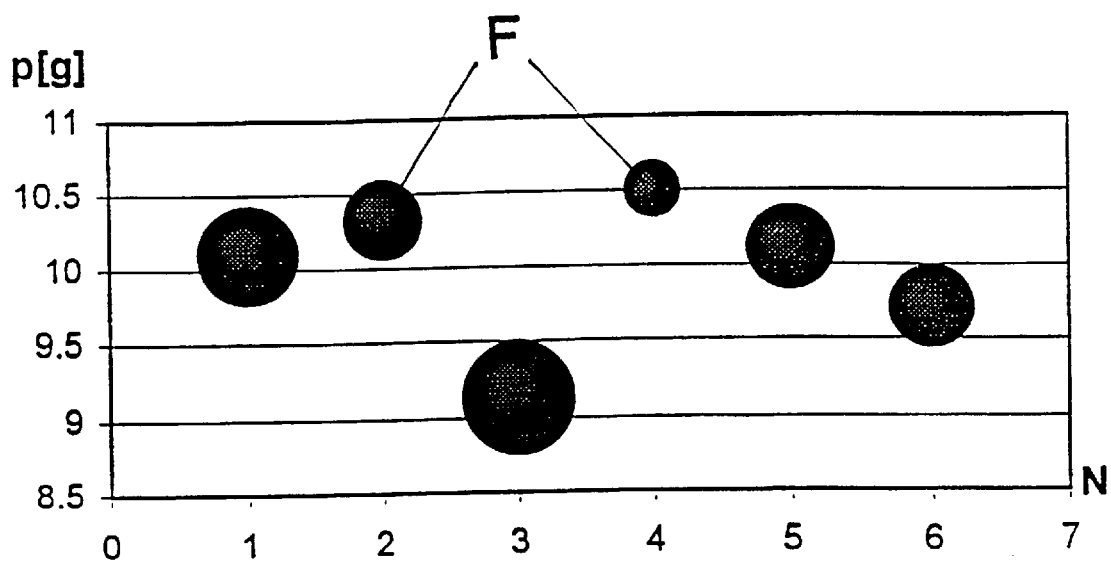
FIG. 3 shows the weight P of strawberries and their intensity represented by areas F as a function of the test numbers N 1 to 7.

The experimental device corresponds to that described under 3.3 A) except that the volume of the container (150 ml) has been adapted to the volume of the sample. Each strawberry of a weight of around 10 g gives a signal of different intensity (Table 2). FIG. 3 shows the weight p of the strawberries and their intensity represented by areas F as a function of the test numbers N 1 to 7.

TABLE 2

| Areas of the signals and statistical evaluation of the results | |
|---|---|
| Weight of the strawberry (g) | Area of the signal |
| 10.1 | 70016 |
| 10.33 | 46320 |
| 9.13 | 91711 |
| 10.51 | 21152 |
| 10.12 | 49966 |
| 9.72 | 49727 |
| Total area | 328,892 |
| Total weight (g) | 59.91 |
| Mean | 54815 |
| Standard deviation | 23862 |
| Coefficient of variation | 43.53% |

C) GLOBAL VOLATILES RELEASED BY DIFFERENT VARIETIES OF STRAWBERRY

The experimental device corresponds to that described under 3.3 A) with the exception of the collection temperature, which is 37° C. The test was conducted in triplicate.

Figure 4:
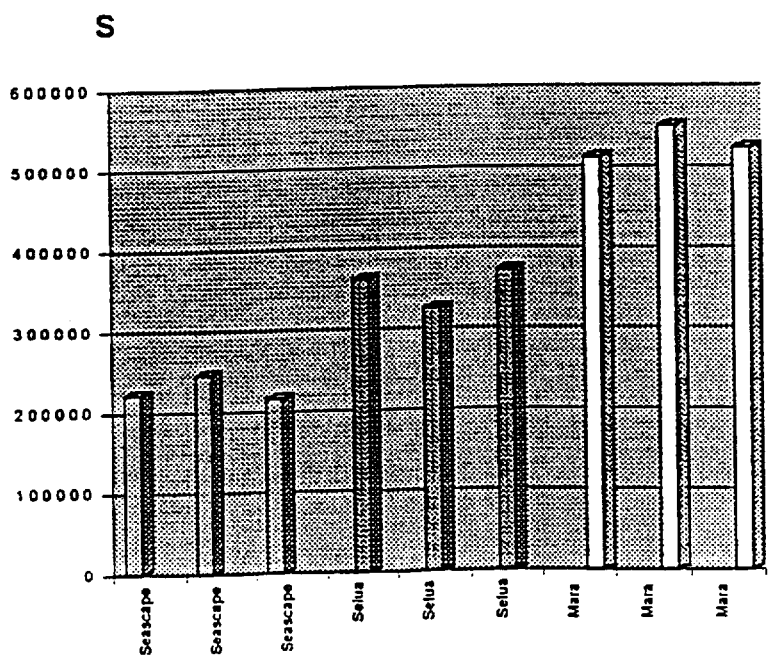
FIG. 4 depicts the area of the signals obtained with the strawberries.

When different varieties of strawberry are measured with the device described above, signals of different areas are obtained for each variety. The sensory analysis, performed by a panel of 10 semi-trained tasters, confirms the fact that the Mara strawberry is distinctly more fragrant than the Seula and Seascape strawberries (Table 3). FIG. 4 depicts the area of the signals obtained with the Seascape strawberries. Seula and Mara also show the reproducibility of the measurement of the global volatiles released. These measurements are therefore in perfect correlation with the sensory analysis.

TABLE 3

Areas of the signals and statistical evaluation for 3 varieties of strawberry

| Variety | Mean | Standard deviation | Coeff. of variation | Brix % | pH |
|---|---|---|---|---|---|
| Seascape | 227,498 | 16,288 | 7.16 | 8.9 | 3.31 |
| Seula | 352,316 | 25,024 | 7.1 | 8.8 | 3.54 |
| Mara | 527,380 | 20,385 | 3.87 | 9.2 | 3.38 |

E) DIFFERENT SPME FIBRES

The experimental device corresponds to that described under 3.3 A). The following SPME fibres (Supelco Co, Bellefonte, Pa.) are used: Polydimethylsiloxane (PDMS), films of different thicknesses, 100, 30, 7 $\mu$m, Polyacrylate (PA) 85 $\mu$m, Carbowax/divinylbenzene (DVB) 60 and 65 $\mu$m and PDMS/carboxene 75 $\mu$m. The use of several fibres makes it possible to create a profile which is a good representation of the volatiles of the product analyzed as a function of the selectivity of the fibre (Table 4).

TABLE 4

Measurement of the global volatiles of the strawberry by different fibres

| Fibres | Signal area |
|---|---|
| PDMS 100 $\mu$m | 131381 |
| PDMS 30 $\mu$m | 45304 |
| PDMS 7 $\mu$m | 40258 |
| PA 85 $\mu$m | 44773 |
| PDMS/DVB 65 $\mu$m | 1587628 |
| PDMS/Carboxene 75 $\mu$m | 2375237 |
| Carbowax/PDMS 65 $\mu$m | 296289 |

F) DIFFERENT KINDS OF HONEY

Figure 5:
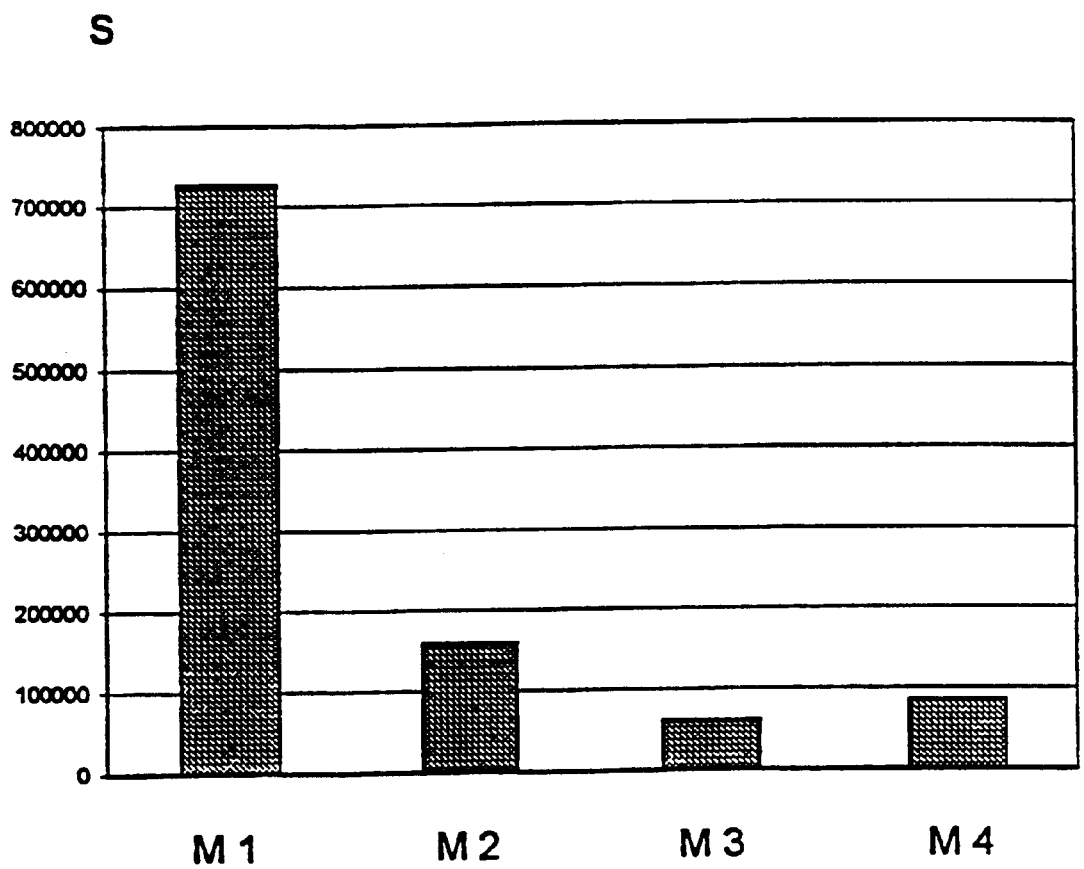
FIG. 5 depicts graphically the area of the signals S as a function of different types of honey M.

The experimental device corresponds to that described under 3.3 A) except that the test is carried out with 60 g of honey, in a 100 ml container. The area of the signal is different for each honey. It corresponds well to the sensory classification of these honeys as regards their aromatic intensity (Table 5). FIG. 5 depicts graphically the area of the signals S as a function of the different types of honey M according to the data in Table 5.

TABLE 5

Measurement of the global volatiles of different honeys

| Name | Area of the signal | Sensory intensity (rank) |
|---|---|---|
| Fir tree honey M1 | 727830 | 1 |
| Country honey M2 | 157894 | 2 |
| Mountain honey M3 | 61297 | 4 |
| Flower honey M4 | 84916 | 3 |

DESCRIPTION OF THE OPERATION OF FIG. 6

The sample to be analyzed 1a is placed in a container 1; the latter is next closed with a lid 1c equipped with a septum 1d. After an equalization time, a collection system 2 resembling a syringe containing an appropriate fibre 2a is introduced through the septum id. Once the guide 2b of the collection system is inside the container, the adsorbent fibre is lowered by means of a plunger 2d. After a time of contact between the fibre and the gaseous phase of the head space 1b, the fibre is raised inside the guide. The collection system 2 is next withdrawn from the container and immediately introduced into the desorption system 3. Once the syringe has been introduced into the desorption system, the fibre is again lowered from the guide using the plunger and desorption takes place under appropriate conditions.

Figure 6:
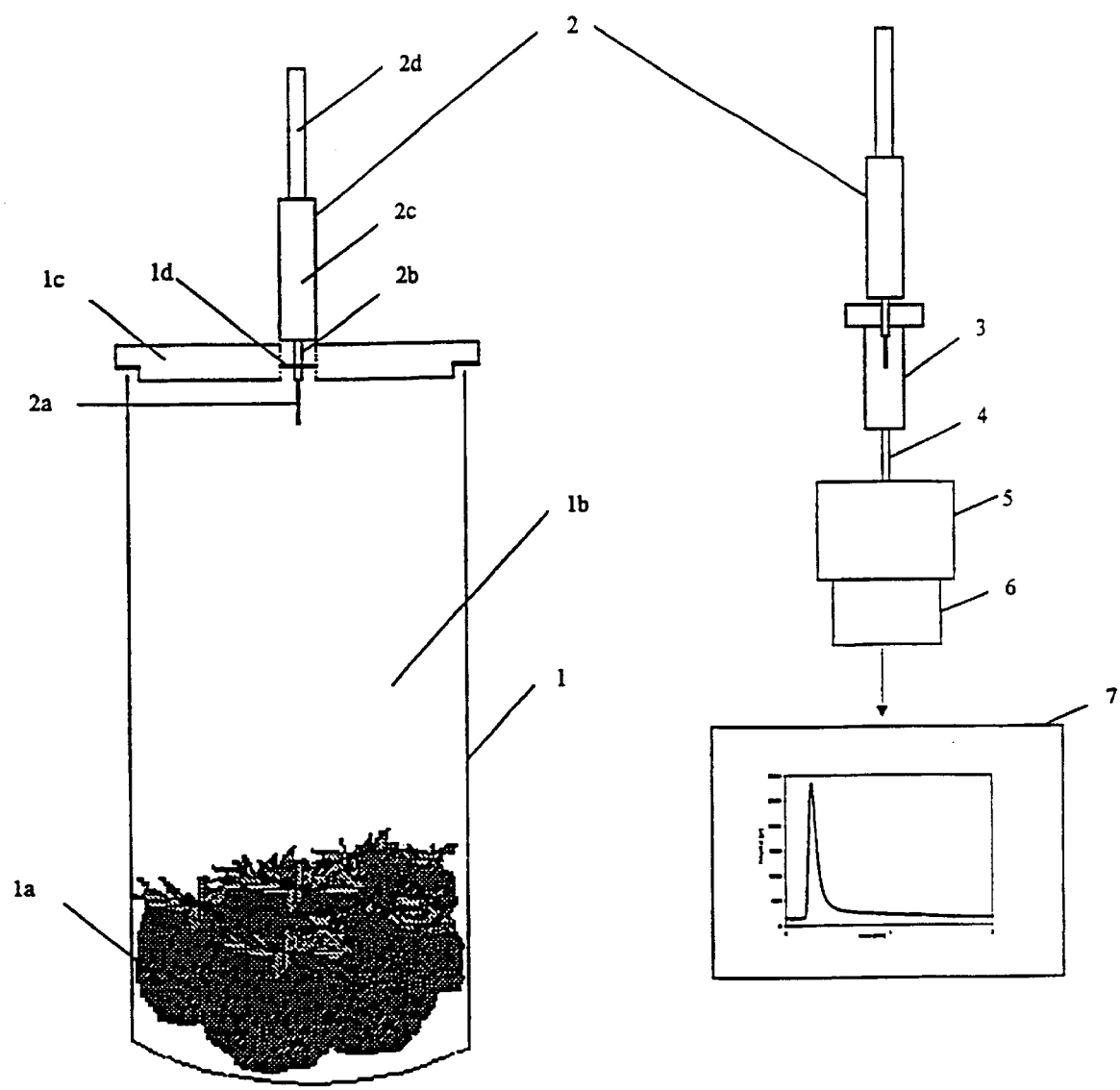
FIG. 6 shows the device and method for measuring volatile substances.

The desorbed volatile substances are transferred by a carrier gas into the detector 5 through a capillary tube 4. The signal from the detector is next processed by an evaluation system 6 and the results are expressed in graphical form 7. LEGEND FOR FIG. 6 "DEVICE FOR MEASURING GLOBAL VOLATILES"

1) Container containing the sample to be analyzed
1a) Sample to be analyzed (strawberries in the present case)
1b) Head space
1c) Lid
1d) Septum
2) Collection system
2a) Fibre
2b) Guide
2c) Syringe body
2d) Plunger
3) Desorption system
4) Capillary tube
5) Detection system
6) Evaluation system for interpreting the signals
7) Results given in the form of a signal

What is claimed is:

1. Method for measuring volatile substances in a global manner, without prior separation of the different compounds, which comprises:

placing a sample to be analyzed in a container with a head space over the sample in the container so that volatile substances are produced in the head space from the sample;

collecting the volatile substances produced in the head space after an equilibration time on a means for collecting the volatile substances which includes adsorption on at least one adsorbent surface introduced into the head space, wherein the means for collecting the volatile substances is based on at least one SPME (Solid Phase Micro Extraction system) and includes an injector with a septum;

removing said adsorbent surface from the head space and transporting the adsorbent surface with collected substances into a desorption system and transferring said collected substances to a detector by one of desorbing said collected substances directly in said detector, and desorbing and conveying said collected substances by means of an inert gas through a capillary tube, wherein said detector detects the volatile substances and produces at least one signal therefrom;

obtaining at least one of a mathematical and statistical analysis of the signal obtained, wherein the analysis is reproducible and correlates with a sensory analysis.

2. Method according to claim 1, wherein the volatile substances comprise the smell of food.

3. Method according to claim 1, wherein the adsorbent surfaces are heated in order to desorb the volatile substances.

4. Method according to claim 1, wherein said signal is transferred from the detector to an evaluation system and the results are expressed in graphical form.

5. Method according to claim 1, wherein the signal is analyzed by measuring at least one of the intensity and shape thereof.

6. Method according to claim 1, wherein the collected substances are conveyed through a capillary tube with substantially no separation thereof.

7. Device for measuring volatile substances in a global manner without prior separation of the different compounds, which comprises:

a container for receiving a sample to be analyzed with a head space therein over the sample in the container for volatile substances produced from the sample;

means for collecting the volatile substances after an equilibration time, including at least one adsorbent surface introduced into the head space, wherein the means for collecting the volatile substances is based on at least one SPME (Solid Phase Micro Extraction system) and includes an injector with a septum;

a desorption system spaced from the container for receiving the adsorbent surface with collected substances;

a detector for receiving the collected volatile substances and producing a signal therefrom; and an evaluation system for receiving said signal and obtaining at least one of a mathematical and statistical analysis of the signal.

8. Device according to claim 7, wherein said desorption system comprises a thermal desorber desorption unit.

9. Device according to claim 8, wherein said desorption unit is programmable.

10. Device according to claim 7, wherein said detector is at least one of a flame ionization detector, thermal conductivity detector, differential resistivity detector, phosphorous nitrogen detector, electron capture detector, and mass spectrometry detector.

* * * * *